United States Patent [19]

Koerner et al.

[11] 4,105,567

[45] Aug. 8, 1978

[54] ORGANOSILICON COMPOUNDS AND TEXTILE FIBER FINISHES CONTAINING THEM

[75] Inventors: Götz Koerner, Essen; Hans-Jürgen Patzke, Gelsenkirchen-Resse, both of Germany

[73] Assignee: Th. Goldschmidt AG, Essen, Germany

[21] Appl. No.: 756,681

[22] Filed: Jan. 4, 1977

[30] Foreign Application Priority Data

Feb. 12, 1976 [GB] United Kingdom ............... 05602/76

[51] Int. Cl.$^2$ ......................................... D06M 13/10
[52] U.S. Cl. ................................ 252/8.6; 106/287.14; 252/8.9; 252/49.6; 260/448.8 R; 428/391
[58] Field of Search ..................... 252/8.9, 8.6, 49.6; 260/448.8 R; 106/287 C; 428/266, 391

[56] References Cited

U.S. PATENT DOCUMENTS

| | | | |
|---|---|---|---|
| 2,838,455 | 6/1958 | Tompkins | 252/8.6 |
| 3,115,512 | 12/1963 | Rossmy et al. | 252/8.9 |
| 3,140,198 | 7/1964 | Dawson et al. | 252/8.9 |
| 3,519,562 | 7/1970 | Lanner | 252/8.8 R |
| 3,634,236 | 1/1972 | Buster et al. | 428/391 |
| 3,968,042 | 7/1976 | Erickson | 428/391 |
| 3,992,332 | 11/1976 | Zenon | 252/8.9 |

*Primary Examiner*—William E. Schulz
*Attorney, Agent, or Firm*—Toren, McGeady & Stanger

[57] ABSTRACT

New organosilicon compounds which are suitable for use in finish compositions for treatment of textile fibers are disclosed. The silicone oils disclosed contain aryloxy and polyether groups and possess excellent thermal stability, compatibility with other substances and antistatic effects. Finish compositions containing the novel silicon compounds of the present invention are also disclosed.

13 Claims, No Drawings

ORGANOSILICON COMPOUNDS AND TEXTILE FIBER FINISHES CONTAINING THEM

BACKGROUND OF THE INVENTION

1. Field of the Invention

The invention relates to new organosilicon compounds. It further relates to preparations for finishing fibers, which contain these new compounds, whereby the preparations are suitable especially for finishing synthetic fibers obtained from melt spinning and, especially, polyester fibers.

2. Description of the Prior Art

Polydimethylsiloxanes are used in spinning plants for finishing melt-spun fibers. Their use for this purpose is possible because of the fact that polydimethylsiloxanes, which are generally referred to simply as silicone oils, endow the treated fibers with a low coefficient of friction, especially at high yarn-take off rates, which coefficient has a slight temperature dependence. In addition, silicone oils are unusually heat stable and have a low viscosity-temperature coefficient.

The finishing of melt-spun yarns directly after their manufacture makes the subsequent drawing and texturizing processes possible. The finish must be effective both as a lubricant and as an antistat. In the thermal fixation processes to which the yarn is subjected, components of the finish are flung off on to the heating unit where they are exposed to heat for a long time. For this reason, the finish must be thermally stable. Those parts of the finish which are deposited on the heating units should, as far as possible, not gel, yellow or evaporate. It is particularly important that there be no gelling.

At the same time, the constituents of the finish should be as compatible as possible with one another. This is a problem especially when it is important to have compatibility between the polar, surface active components, which are primarily responsible for the antistatic effect, and the nonpolar methylsilicone oils, which are primarily responsible for the lubricating properties.

The compatibility of methylsilicone oils can be improved if the methyl groups are partially replaced by longer-chained alkyl groups. The resulting oils are then, however, no longer sufficiently stable thermally. In addition, the viscosity-temperature coefficient of methyl-silicone oils which are modified in such a manner increases greatly.

Even the partial replacement of methyl groups by phenyl groups leads to products with higher viscosity-temperature coefficients whose lubricating properties are impaired.

SUMMARY OF THE INVENTION

Surprisingly, certain silicone oils containing aryloxy and polyether groups proved to have particularly good thermal stability and excellent compatibility with other substances. At the same time, these products showed a clear improvement over the normal silicone oils with regard to their antistatic effect.

Silicone polyethers have already been used as fiber-treating materials, for example, as disclosed in the German Auslegeschrift No. 1,594,986 and in German Auslegeschrift No. 1,719,365. These products still, however, possess thermal stabilities which are much too low. They are thus not well suited for use in melt-spin finishes (100% or as additives).

The new organosilicon compounds of the present invention correspond to the general formula

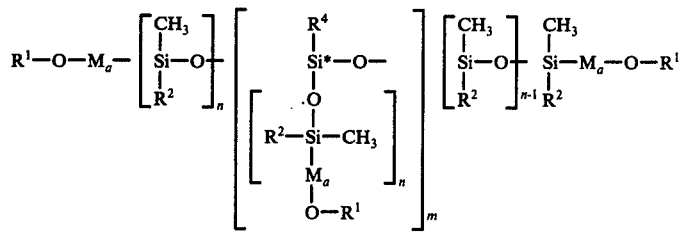

This formula represents an average formula of a polymer mixture.

In this formula $R^1$ may represent an alkylated phenyl residue with mono-, di-or trialkylphenyl residues which contain 6 to 12 aliphatically linked carbon atoms being preferred. Especially preferred are the modifications in which $R^1$ represents an octyl, dodecyl- or nonylphenyl residue, and, in turn, the nonylphenyl residue is the most suitable residue.

The octyl, dodecyl- and nonylphenyl residues are introduced into the siloxanes by using commercially available octyl, dodecyl or nonylphenols as starting materials. These are obtained by reacting phenol with diisobutylene, tetrapropylene or tripropylene.

Within this definition, however, the $R^1$ residue can also represent a 2,6-di-iso-propylphenyl, 2,6di-iso-butylphenyl or a 2,6-di-tert.-butylphenyl group.

$R^1$ can also represent a polyether residue corresponding to the formula

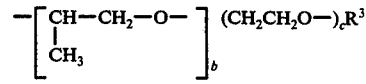

in which $R^3$ is an alkyl residue with 1 to 16 carbon atoms, an acyl residue with 1 to 12 carbon atoms, or, if necessary, a hydrocarbon substituted phenyl residue.

However, mono-, di- or trialkylphenyl residues which contain 6 to 12 aliphatically linked carbon atoms are preferred.

In an especially preferred version, $R^3$ represents an octyl, dodecyl or nonylphenyl residue, and the nonylphenyl residue is the most preferred residue, and wherein $b$ has a value from 0 to 2, preferably 0, and $c$ has a value of 1 to 30; or $R^1$ can also be a trimethylsilyl residue.

M is an alkylene residue with 1 to 3 carbon atoms.

$R^2$ may represent an alkyl residue with 1 to 16 carbon atoms, wherein the carbon chain may be interrupted by the groupings

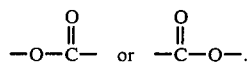

Preferably,
$R^2$ represents a methyl residue. Further examples of suitable residues are: $C_2H_5-$, $C_3H_7-$, $C_{10}H_{21}-$, $C_{12}H_{25}-$, $-(CH_2)_2OAc$, wherein
Ac = saturated aliphatic acyl residue with 1 to 12 carbon atoms, e.g.,

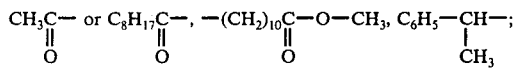

or
$R^2$ can also represent the $M_aO-R^1$ residue wherein $R^1$ is as defined above and $a$ is defined below;
$R^4$ is an alkyl residue with 1 to 16 carbon atoms and preferably is a methyl residue; or a group having the formula

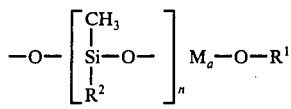

wherein $R^1$ and $R^2$ and M are as defined above, and $a$ and $n$ are as defined hereinbelow.
The indices have the following meaning:
  $m$ has a value of 0 to 5, preferably, however 0, in which case the compound is a linear organosilicon.
  $n$ has a value of 2.5 to 20, preferably 5 to 12.5.
  $a$ has a value of 0 or 1, preferably,
    $a = 0$, in which case, the alkylated phenyl, polyether, or the trimethylsilyl residue is linked via an oxygen atom to the neighboring silicon atom.
In addition, the following restrictions apply to the average molecule:
The average molecule shall have 5 to 40 Si atoms. There must be at least 0.2 and at most 5, if necessary, alkylated phenyl residues in the molecule which are linked via the $Si-M_a-O$ grouping directly to Si atoms, and at least 0.2 and, at most, 5 polyalkyleneglycol units must be present.
Preferably, the molecule does not contain any Si* atoms, i.e., preferably, $m$ is not equal to 0. Also, it is preferred that the molecule contains 0.4 to 2.0 alkylated phenyl residues which are linked via the $Si-M_a-O$ grouping directly to the Si atoms, the average molecule contains 0.4 to 2.0 polyether residues, and 10 to 25 Si atoms.

DESCRIPTION OF THE PREFERRED EMBODIMENT

The new silicone polyethers are mixtures for which, however, average formulas can be given. The distribution of the alkylated phenyl residues, which are linked via the $Si-M_a-O$ grouping directly to the Si atoms, and of the phenylalkyleneglycol blocks is determined by the synthesis conditions and, preferably, is a statistical distribution.
The following further examples of compounds according to the invention are within the scope of the above formula. From the point of view of their properties, they are especially preferred for treating fibers:

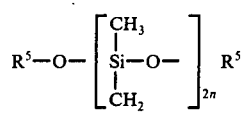     II wherein
20 to 80 mole % of the $R^5$ residues are

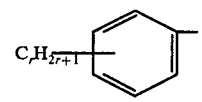

residues, whereby the $C_rH_{2r+1}$ substituent is mainly in the para position.
  $r$ is a number from 8 to 12,
  $n$ is a number from 5 to 12.5 or wherein
  20 to 80 mole % of the $R^5$ residues are

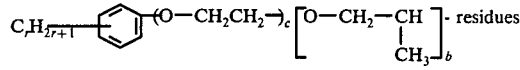 - residues wherein
  $b$ is a number from 0 to 2, and preferably is 0,
  $c$ is a number from 1 to 30, and preferably is from 5 to 15.

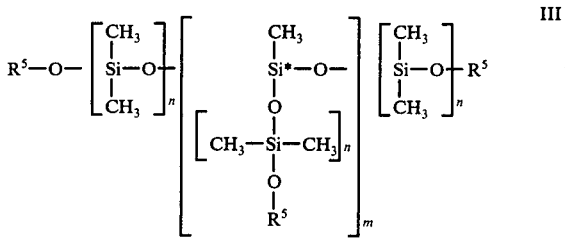     III wherein
$R^5$ is as defined above,
$n = 2.5$ to 13, and preferably is 4 to 8,
$m = 1$ to 5
whereby 10 to 40 and, preferably, 10 to 25 Si atoms are contained per molecule of which, however, not more than 20 mole % of the Si atoms consist of Si* atoms.

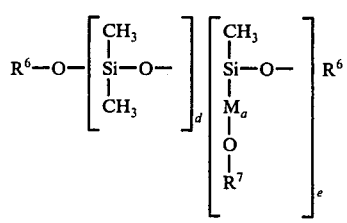     IV wherein
$R^6$ is the $(CH_3)_3Si$-residue or

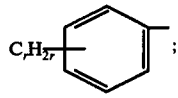

$R^7 = R^5$, if $R^6$ is a $(CH_3)_3Si$-residue,
$R^7$ is a

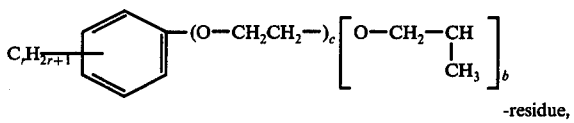
-residue, if $R^6$ is a

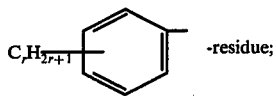 -residue;

$R^5$, $r$, $b$, and $c$ are as defined above,
$d = 2.5$ to 37.5, and preferably is 7.5 to 22.5,
$e = 0.5$ to 10, and preferably is 2 to 5,
$M = -CH_2CH_2-$ or $-CH_2CH_2CH_2-$,
$a = 0$ or 1, and preferably is 0
and there is present per molecule 10 to 40, and preferably, 12 to 25 Si atoms.

The chemical stability of the inventive silicone polyether decreases with increasing polyether content. On the other hand, the compatibility and the antistatic effect of the inventive silicone polyether increase with increasing polyether content. Depending on the application, an optimum balance can be selected. Typical polyether contents lie between 20 and 60% by weight.

Depending on the selection of the polyether and aryloxy substituent, miscibility gaps can occur in the polymer mixture resulting in cloudy products. In general, homogeneous products are preferred.

Surprisingly, it has now been found that the incorporation of certain aryl groups, which are linked via Si—$M_a$—O bonds directly to Si atoms, significantly improve the stability of the silicone polyethers.

The synthesis of the inventive compounds can be successfully carried out by known methods. The inventive compounds, in which the alkylated phenyl residues or the polyethers which are linked directly to the Si atoms are connected via SiOC bonds to the siloxane molecule, can be synthesized by a large number of known procedures. They are particularly readily synthesized by reacting the appropriate phenols of polyether monools with equilibrated chlorosiloxanes or chlorosiloxanyl sulfates, using suitable acid acceptors and the procedure disclosed in U.S. Pat. No. 3,115,512.

A further known path to this type of inventive compound involves reacting appropriate phenols or polyether monools with equilibrated siloxanes containing SiH bonds whereby the linking takes place with elimination of hydrogen. In this type of reaction, the use of suitable catalysts, such as, Sn octoate, is logical. Processes of this kind are shown in the British Pat No. 954,041, with the difference that in the disclosure in that patent, only polyether monools, e.g., arylpolyether monools, and (alkyl)-phenols are not used at the same time as reaction partners.

The inventive compounds in which the mono-, di- or trialkylphenyl residues are linked to the siloxane molecule via SiC bonds can be synthesized, for example, by the addition of allyl or vinyl ethers of the appropriate phenols or polyether monools to siloxanes, containing SiH bonds, using Pt catalysts, such as, $H_2PtCl_6$, according to the following reaction sequence:

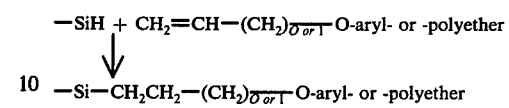

This reaction is very common for the synthesis of the so-called "organofunctional siloxanes." An example of such an addition of siloxanes, containing SiH groups, to polyethers containing an alkenyl group, is described in U.S. Pat. No. 2,868,824.

A further synthesis method consists of reacting siloxanes with -SiCH$_2$-halogen groups with the appropriate phenols or polyether monools in the presence of acid acceptors. According to the following reaction outline

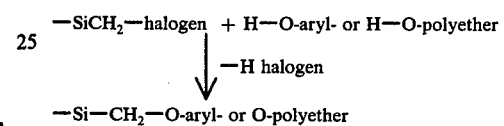

aryloxy or polyether substituted siloxanes are formed, which are linked via a CH$_2$ group. Such a process is described on Page 321 of the Monograph of W. Noll, "Chemie und Technologie der Silicone (Chemistry and Technology of the Silicones)," published in 1968 by Chemie, where the phenolic component 4,4'-dihydroxydiphenylpropane is used, which is not in accordance with the invention.

The above processes, mentioned as examples of the synthesis of the inventive compounds, can also, of course, be used side by side in one and the same polymer molecule.

When strong acids are used for equilibrating the starting products, it is logical to free the end products as far as possible from the residues of these strong acids, since these can have a negative effect on the thermal stability of the end products, especially, with regard to yellowing.

The invention furthermore relates to textile-fiber finishes, especially melt-spin finishes, which contain the inventive organosilicon compounds (referred to in the following as the substances of Group A).

In addition to the inventive compounds of Group A, the finish composition may contain, if necessary, members of a group of substances which are nonpolar and have a favorable effect on the lubricating properties even at high yarn-take-off rates. This group (hereinafter designated as Group B) includes, for example, the so-called ester oils, such as, fatty acid esters of polyols. Representatives of such compounds are trimethylolpropane tripelargonate or pentaerythritol tetrapelargonate or esters of monools, such as, hexadecyl stearate, butyl stearate, or oleyl oleate. Dialkyl phthalates can also be described as ester oils. Dialkyl phthalates of special interest are those which are derived from branched secondary or primary alcohols. Mineral oils or liquid, oligomeric polyolefins are pricewise more favorable finish components. Such finish components are, however, inferior to ester oils which regard to their thermal stability.

Hydrophobic polypropylene glycols may also be regarded as essentially nonpolar components which, however, in comparison with ester oils possess disadvantages with regard to their thermal load-carrying capacity. Certain aryloxy-modified silicone oils have advantages over ester oils with regard to their thermal load-carrying capacity and over silicone oils with regard to an improved compatibility.

These modified silicone oils are described in the British Provisional Application 50 681/75. They are compounds of the general formula

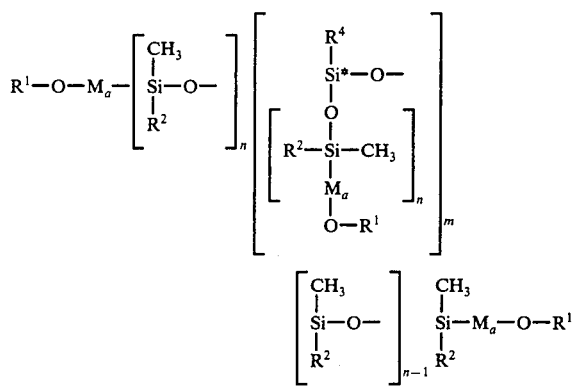

in which

R$^1$ is a mono-, di- or trialkylphenyl residue, in which the number of the carbon atoms per phenyl residue, bound in the form of alkyl residues, is at least 6 and at most 12;
or the trimethylsilyl residue.

R$^2$ is an alkyl residue with 1 to 16 carbon atoms, whereby the carbon chain may be interrupted by the groupings

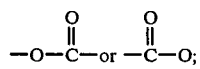

or the M$_a$—O—R$^3$ residue, whereby R$^3$ is a mono-, di- or trialkylphenyl residue wherein the number of the carbon atoms per phenyl residue bound in the form of alkyl residues, is at least 6 and at most 12; or is the

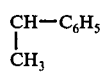

residue;

R$^4$ is an alkyl residue with 1 to 16 carbon atoms or

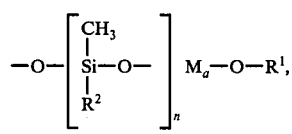

and preferably is CH$_3$,

M is an alkylene residue with 1 to 3 carbon atoms, the indices $n$ may have any avlue from 2.5 to 15, $m$ has a value of 0 to 5, $a$ has a value of 0 or 1, and the average molecule contains 5 to 30 Si atoms, of which at most 20 mole percent are Si* atoms, and 0.5 to 10 mono-, di- or trialkylphenyl residues.

These aryloxy modified silicone oils are also to be regarded as belonging to the group of nonpolar melt-spin finish components and endow the finishes with a particularly high thermal stability.

Compounds of the formula

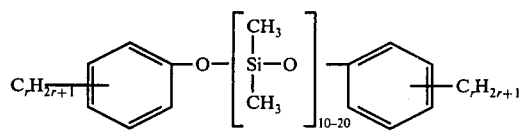

wherein $r = 8$ to 12 are especially preferred for mixing in with the polyether siloxanes of the present invention.

As a rule, the viscosities (at 20° C) of the nonpolar or weakly polar oils of this Group B lie between 5 and 100 cP, preferably, between 10 and 60 cP.

Melt-spin finishes frequently contain polar components, which can be subdivided into Groups C and D, according to whether their polarity is more or less strongly marked.

The task of the moderately polar, nonionic components of the Group C is, inter alia, to improve the antistatic effect and, if necessary, to improve the compatibility of the nonpolar components (Group B) with the strongly polar, ionic components (Group D). The latter components are customarily used especially as antistatic agents.

Typical representatives of nonionic finish components are water-soluble or water-dispersible ethylene oxide adducts of fatty acids, fatty alcohols, fatty amines or fatty acid amides wherein the liquid, low viscosity representatives of this group are preferred. Especially suitable is $C_{12}H_{25}N(CH_2CH_2OH)_2$, wherein the $C_{12}H_{25}$-residue represents a mixture of $C_8H_{17}$—, $C_{10}H_{21}$—, $C_{12}H_{25}$—, $C_{14}H_{29}$—, $C_{16}H_{33}$— and $C_{18}H_{37}$—residues. The OH groups may be completely or partially esterified or etherified. Ethylene oxide adducts of polyesters of fatty acids, such as, glycerol or sorbitol esters, e.g., sorbitol monooleate or glycerol trioleate, are also suitable.

The ethylene oxide adducts of alkylphenols, such as, for example, nonylphenol, represent nonionic components of finishes which are especially stable thermally. Other polyethylene glycol monoaryl ethers are also suitable as finish components which are especially thermally stable, wherein the aryl residue can be a phenyl residue.

In the final analysis, the silicone polyethers of the present invention also belong to the moderately polar, nonionic components of the Group C. These polyethers have been segregated here into a special Group A, because of their exceptional thermal stability and their lubricating properties.

The highly polar finish components of Group D which usually consist of liquid organic surfactants having ionic groups, can be anionic, amphoteric or cationic.

These compounds have attained importance especially as antistatic additives. Typical anionic surfactants of this group are alkali salts of alkyl phosphates or alkyl phosphonates, e.g., Na octyl-1½-phosphate. In addition, sulfated mineral oils or fatty alcohol sulfates or alkylpolyether sulfates can also be used. The alkali salts of the unsaturated fatty acids also belong to this group.

Further representatives of this group are the alkali salts of alkyl benzene sulfonates. Typical amphoteric surfactants of this group are the surface active betaines.

The cationic surfactants have achieved particular importance as components of melt-spin finishes. Typical representatives of this group are the alkyltrimethyl ammonium sulfates, e.g., the trimethylammonium methyl sulfate of coconut oil. Especially suitable is

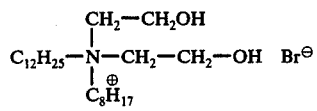

for which the $C_{12}H_{25}$ residue consists of the statistical average of $C_8-$, $C_{10}-$, $C_{12}-$, $C_4-$, $C_{16}-$ and $C_{18}$ components. The OH groups may be partially or completely esterified or etherified. Because of the slight thermal stability of the highly polar components of Group D and because of their poor compatibility, only the minimum amounts required of these compounds are taken. Antistatically active compounds of Group C and D are described comprehensively by W. Biedermann, "Plaste und Kautschuk (Plastics and Rubber)," 16, 8–15 (1969) as well as by L. R. Kumar in Silk, Rayon Ind., India 12 315 – 333 (1969).

The present invention therefore relates to melt-spin finishes which consist of:
- 5 – 100% by weight of the modified silicone oils of Group A;
- 0 – 90% by weight of the nonpolar or weakly polar oils of Group B;
- 0 – 30% by weight of the nonionic compounds of Group C;
- 0 – 15% by weight of ionic surfactants of Group D; and if necessary, conventional additives; wherein the sum of the components adds up to 100% by weight.

At the same time, compositions are preferred which consist of:
- 10 – 70% by weight of the inventively modified silicone oil of Group A;
- 40 – 90% by weight of the nonpolar or weakly polar oils of Group B;
- 0 – 20% by weight of the nonionic compounds of Group C;
- 0 – 10% by weight of the ionic surfactants of Group D;

and if necessary, conventional additives, wherein the sum of the components adds up to 100% by weight.

Especially preferred is a finish which is composed of:
30 – 95% by weight of a siloxane having the formula

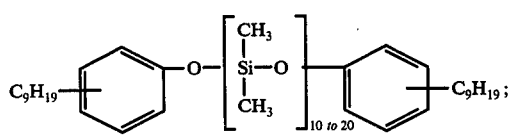

3 – 70% by weight of compounds having structural formula I; and
0 – 30% by weight of $C_{12}H_{25}-N-(CH_2CH_2OH)_2$.
Equally preferred is a finish consisting of:
8 – 95% by weight of a siloxane having the formula

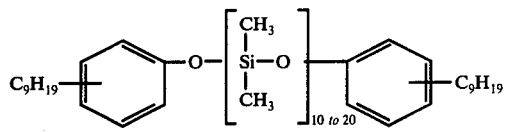

3 – 90% by weight of compounds having structural formula I;
1.5 – 30% by weight of $C_{12}H_{25}-N-(CH_2CH_2OH)_2$; and
0.5 – 10% by weight of

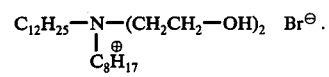

Depending on the nature of the application, these substances can be used in the above described mixture in the undiluted state or diluted in the form of solutions, whereby hydrocarbons are the preferred solvents, or in the form of emulsions, in which case, additional suitable emulsifiers which are conventional in the art can be used. Other conventional additives, appropriate to the state of the art, such as, oxidation inhibitors, for example, phenols (e.g. dicresylpropane) or sodium hypophosphite, can also be added to these finishes.

The inventive preparations distinguish themselves, in comparison with preparations known to the art which contain conventional silicone polyethers, by exhibiting decreased gelling and yellowing tendencies during prolonged heating at 200° C and above.

On the basis of good compatibility of the inventively useable silicone polyethers within the scope of the compositions shown, it is especially noteworthy that it is possible to prepare solvent-free melt-spin finishes which are self-emulsifiable and which are therefore readily washed out, and yet, at the same time, they exhibit good compatibility. Such solvent-free 100% finishes represent an advance over solutions and emulsions with regard to their decreased contamination effect on the environment.

In the following examples, the synthesis of the inventive compounds is described as well as is their use in the treatment of fibers.

EXAMPLE 1 (Synthesis Process 1)

415.8 g (0.63 equivalent) of a nonylphenol polyether of the formula

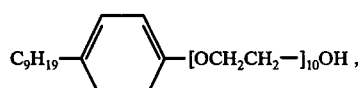

92.4 g (0.42 equivalent) nonylphenol and 2750 ml toluene are added to the reaction flask. While stirring, 550 ml toluene are distilled off for the purpose of azeotropic drying. The contents of the flask are brought to 50° C and treated with 598.5 g (1.0 equivalent) of a siloxane of the average formula

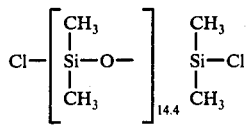

Stirring is continued for a further 30 minutes at 50° C. At the same temperature, ammonia is then passed in until the reaction turns alkaline. Stirring is then continued for a further 30 minutes under a mild atmosphere of NH₃ and the temperature is subsequently lowered to below 30° C. The mixture is subjected to an intermediate filtration through a filter layer of cellulose fibers. The clear filtrate is returned to the flask which is then evacuated.

While stirring vigorously, all the distillate is removed until the contents of the flask reach a temperature of 100° C. When the distillation ceases, stirring is continued for a further 30 minutes at a flask content temperature of 100° C and under vacuum (20 mm Hg). The contents of the flask are then cooled to ca. 30° C and the vacuum is released. The reaction mixture is filtered again through a filter layer of cellulose fibers. The clear product thus produced, was colored yellow and had a viscosity (20° C) of 176 cP.

The product corresponds to the material labeled No. 1 in the table below.

EXAMPLE 2 (Synthesis Process 2)

350 g (0.50 equivalent) of an allylated nonylphenolpolyether of the formula

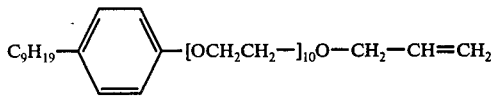

are added to the reaction flask and heated to a temperature of 120° C. (The allylated nonylphenol polyether is synthesized according to a known procedure in that initially, ethylene oxide is added to nonylphenol and the product is subsequently allylated with allyl chloride, using sodium as acid acceptor.)

While stirring at this temperature, 7.25 mg of pyridine (C₂H₄) PtCl₂ were added. Subsequently, 241.6 g (0.50 equivalent) of a siloxane having the average composition

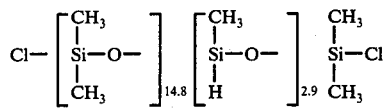

are added dropwise, initially at only a slow rate. Only when the reaction has commenced (this can be seen by a rise in the temperature of the reaction mixture), is the rate of dropwise addition increased in such a way that the addition is completed with 2 hours.

Stirring is subsequently continued for 3 hours at a bath temperature of 120° C and the reaction mixture is then cooled to 50° C. The reaction mixture contains 0.583 equivalents of hydrolyzable chloride per kg. 1338 ml dry toluene and 77.4 g (0.352 equivalents) nonylphenol are now added. Ammonia is then passed in at the same temperature until the reaction turns alkaline. Stirring is continued for a further 30 minutes under a mild cover of ammonia and the temperature is subsequently lowered to below 30° C. Now follows an intermediate filtration through a filter layer of cellulose fiber. The filtrate is returned to the flask, which is then evacuated. While stirring vigorously, all the distillate is taken off until the contents of the flask reach a temperature of 100° C.

When the distillation ceases, stirring is continued for a further thirty minutes with the contents of the flask at a temperature of 100° C under a vacuum (20 mm Hg). The contents of the flask are then cooled to ca. 30° C and the vacuum is released. The reaction mixture is again filtered through a filter layer of cellulose fiber. A slightly cloudy, yellow product is obtained.

This product corresponds to the material labeled No. 6 in the table below.

EXAMPLE 3 (Synthesis Process 3)

165 g (0.25 equivalent) of a nonylphenolpolyether of the formula

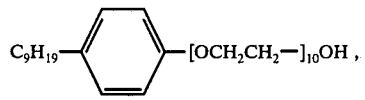

55.0 g (0.25 equivalent) of nonylphenol and 545 ml toluene are added to the reaction flask. While stirring, 182 ml toluene are distilled off for the purpose of azeotropic drying. The contents of the flask are brought to a temperature of 90° C and treated with 0.95 g Sn octoate. Thereupon, while maintaining an internal temperature of 95° C, 143 g (0.50 equivalent) of a siloxane having the average composition

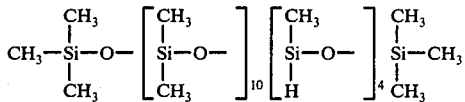

are added dropwise during 2 hours. There is a vigorous evolution of hydrogen during this time.

After completing the addition of the siloxane, the temperature is raised to 140° during 20 minutes and maintained there for 5 hours under reflux, while stirring vigorously. Subsequently, all the distillate is taken off until the contents of the flask reach a temperature of 140° C under a water vacuum. When the distillation ceases, stirring is continued for a further 30 minutes, while the contents of the flask are at a temperature of 140° C and under vacuum (20 mm Hg). The contents of the flask are then cooled to ca. 30° C and the vacuum is subsequently released. The reaction mixture is filtered through a filter layer of cellulose fiber. A pale yellow, clear product is obtained. This product corresponds to the material labeled No. 7 in the following table.

Useable products in accordance with the present invention (Nos. 1 - 10) are assembled in the following table according to their formula, synthesis process and properties. Under Nos. 11 - 16, products are listed which are not in accordance with the invention while products are shown under 17 and 18, which can be used as inventive melt-spin finishes.

| No. | R¹ | M | a | R² | n | m | Number of Si atoms/mole | Viscosity (20° C in cP) | Synthesis Process |
|---|---|---|---|---|---|---|---|---|---|
| 1 | 1.2 C₉H₁₉—⌬—[OCH₂CH₂—]₁₀ and 0.8 nonylphenyl- | — | 0 | CH₃— | 7.7 | 0 | 15.4 | 176 | 1 |
| 2 | 1.4 C₉H₁₉—⌬—[OCH₂CH₂—]₁₀ and 0.6 nonylphenyl- | — | 0 | CH₃— | 7.7 | 0 | 15.4 | 199 | 1 |
| 3 | 1.2 C₉H₁₉—⌬—[OCH₂CH₂—]₁₀ and 0.8 nonylphenyl- | — | 0 | CH₃— | 6.0 | 0 | 12.0 | 253 | 1 |
| 4 | 1.2 C₈H₁₇—⌬—[OCH₂CH₂—]₁₀ and 0.8 nonylphenyl- | — | 0 | CH₃— | 7.4 | 0 | 14.8 | 154 | 1 |
| 5 | 1.2 C₉H₁₉—⌬—[OCH₂CH₂—]₁₀ and 0.8 phenyl-Nonylphenyl | — | 0 | CH₃— | 7.5 | 0 | 15.0 | 179 | 1 |
| 6 | 1.5 C₉H₁₉—⌬—[OCH₂CH₂—]₁₀ and 1.5 nonylphenyl nonylphenyl | — | 0 | 15.8 CH₃— and 2.9 C₉H₁₉—⌬—[OCH₂CH₂—]₁₀O—(CH₂)₃— | 9.35 | 0 | 18.7 | 1046 | 2 |

| No. | R¹ | M | a | R² | R⁴ | n | m | Number of Si atoms/mole | Viscosity (20° C in cP) | Synthesis Process |
|---|---|---|---|---|---|---|---|---|---|---|
| 7 | (CH₃)₃—Si— | — | 0 | 10 CH₃—, 2 nonylphenoxy- and 2 C₉H₁₉—⌬—[OCH₂CH₂—]₁₀O— | — | 7.0 | 0 | 16.0 | 592 | 3 |
| 8 | 1.2 CH₃—[OCH₂CH₂—]₁₀ and 0.8 nonylphenyl- | — | 0 | CH₃— | — | 7.7 | 0 | 15.4 | 131 | 1 |
| 9 | 1.5 C₉H₁₉—⌬—[OCH₂CH₂—]₁₀ | — | 0 | CH₃— | CH₃—5.0 | 5.0 | 1 | 16.0 | 363 | 1 |
| 10 | and 1.5 nonylphenyl nonylphenyl | — | 0 | 15.8 CH₃— and 2.9 CH₃—C—O—[CH₂CH₂O—]₁₀(CH₂)₃—  ‖  O | — | 9.35 | 0 | 18.7 | 416 | 2* |

| No. | R¹ | M | a | R² | R² | n | m | Number of Si atoms/mole | Viscosity (20° C in cP) |
|---|---|---|---|---|---|---|---|---|---|
| 11 | Commercial product, siloxane | | | | | | | | |

-continued

| | | | | | | | | |
|---|---|---|---|---|---|---|---|---|
| 12 | portion (50% by weight); the polyoxyalkylene segments (formed from ethyleneoxide chains) are combined with the polydimethylsiloxane segments by SiC bonds Commercial product, siloxane portion (30% by weight) constructed as No. 11 | — | — | — | — | — | — | −380 |
| 13 14 | — | $CH_3-[OCH_2CH_2-]_{10}$ $C_9H_{19}\text{-}\phantom{xxx}\text{-}[OCH_2CH_2-]_{10}$ | 0 0 | $CH_3-$ $CH_3-$ | 6.1 6.0 | 0 0 | 12.2 12.0 | −590 112 286 |
| 15 16 | Methylsilicone oil, 25cP Trimethylolpropane | — | — | — | — | — | — | 25 |
| 17 | Tripelargonate Mixture of: 15% 1.), 5% $C_{12}H_{25}-N-(CH_2CH_2OH)_2$ and $C_9H_{19}\text{-}\phantom{xxx}\text{-}O-\left[\begin{array}{c}CH_3\\|\\Si-O\\|\\CH_3\end{array}\right]_{12}\text{-}\phantom{xxx}\text{-}C_9H_{19}$ | — | — | — | — | — | 45 69 69 |
| 18 | Mixture of: 37% 1.), 13.5 % $C_{12}H_{25}-N-(CH_2CH_2OH)_2,$ 4.5%

$\begin{array}{c}CH_2-CH_2OH\\|\\C_{12}H_{25}-N-CH_2-CH_2OHBr^{\ominus}\\|\oplus\\C_8H_{17},\end{array}$ and 45%

$C_9H_{19}\text{-}\phantom{xxx}\text{-}O-\left[\begin{array}{c}CH_3\\|\\Si-O\\|\\CH_3\end{array}\right]_{12}\text{-}\phantom{xxx}\text{-}C_9H_{19}$ | — | — | — | — | — | 119 |

*The allylpolyether acetate used here is synthesized by a known process. Initially, ethylene oxide is added to allyl alcohol and the product is subsequently acetylated with acetic anhydride. In other respects, the procedure is analogous to synthetic process 2.
Products 11 to 16 are not of the invention.
Products 11 and 12 are commercial silicone polyethers, which are offered as melt-spin finish components.

| No. | Volatile Components (3g sample; metal dish, 5.2 cm diam, 16 hr at 200° C., circulating air) in % by weight | Gelling time (hr) at 200° C | Compatibility of the following mixtures: | | | The actual antistatic property is expressed by a scale falue which extends from 6 - 12 and which was obtained from surface conductivity measurements in combination with practical resuts. The values have the following significance 6 – 9 very good 9 – 10.5 good > 10.5 not adequate | Coefficient of friction μ (fiber/metal; take-off rate 100 m/min; polyester yarn) |
|---|---|---|---|---|---|---|---|
| | | | 18¾ wt.% active material 81¼ wt.%* | 16.7 wt.% active material 72.2 wt.%* 11.1 wt.%** | 15.0 wt.% active material 65.0 wt.%* 10.0 wt.%** 10.0 wt.%*** | | |
| 1 | 45.2 | 48 | clear | clear | clear | 10.3 | 0.22 |
| 2 | 49.3 | 36 | clear | clear | clear | 10.2 | — |
| 3 | 54.6 | 23 | clear | clear | clear | 10.2 | — |
| 4 | 51.7 | 24 | clear | clear | clear | 10.3 | — |
| 5 | 51.8 | 16 | clear | clear | clear | — | — |
| 6 | 34.9 | 16 | slightly cloudy | slightly cloudy | slightly cloudy | — | — |
| 7 | 56.2 | 12 | clear | clear | clear | — | — |
| 8 | 51.0 | 12 | clear | cloudy | clear | 10.3 | — |
| 9 | 47.5 | 16 | clear | clear | clear | 10.2 | — |
| 10 | 57.5 | 12 | slightly cloudy | slightly cloudy | clear | 10.2 | — |
| 11 | 61.8 | 2 | cloudy | cloudy | slightly cloudy | 10.2 | 0.22 |
| 12 | 55.8 | 2 | — | — | — | — | 0.24 |
| 13 | 68.5 | 3 | slightly cloudy | slightly cloudy | clear | — | — |
| 14 | 61.1 | 7 | clear | clear | clear | — | — |
| 15 | 32.6 | >500 | not miscible | not miscible | not miscible | 12.2 | 0.20 |
| 16 | 36.5 | 24 | clear | not miscible | clear | 12.4 | 0.25 |
| 17 | 29.0 | >200 | — | — | — | 10.4 | 0.22 |
| 18 | 46.0 | 24 | — | — | — | 8.5 | 0.22 |

*Trimethylolpropane Tripelargonate

** 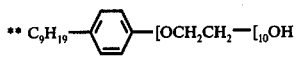$C_9H_{19}$—⟨ ⟩—[OCH$_2$CH$_2$—]$_{10}$OH

***Mixture of 50% by weight: $C_{12}H_{25}$—N—(CH$_2$CH$_2$OH)$_2$ and 50% by weight:

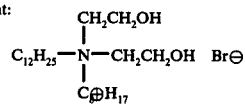

The data in the tables illustrates the following:

The silicone polyethers of the present invention (Nos. 1 to 10) are superior with regard to their content of volatile constituents and, especially, with regard to their resistance to gelling as compared to the commercial silicone polyethers (Nos. 11 and 12) and the silicone polyethers (Nos. 13 and 14) which are not in accordance with the invention. The test by which the content of volatile constituents was determined, corresponds to the conventional procedure. A very similar procedure is described, for example, in the U.S. Pat. No. 3,578,594, in Column 15, Paragraph 1, Line 4. Compared to the thermally stable silicone oil, the inventive silicone polyethers are significantly more compatible. (Silicone oils of this type can generally not be used because of their incompatibility.)

In addition, it is evident from the table that the silicone polyethers show a significantly better antistatic effect than the silicone oils. The ester oil (trimethylolpropane tripelargonate), listed under No. 16, is inferior with regard to its antistatic effect, lubricating properties and miscibility. Nos. 17 and 18 illustrate how finishes with superior thermal stability can be prepared from the inventive silicone polyethers. No. 18 shows a finish with a very good antistatic effect.

What is claimed is:

1. Compounds of the general formula

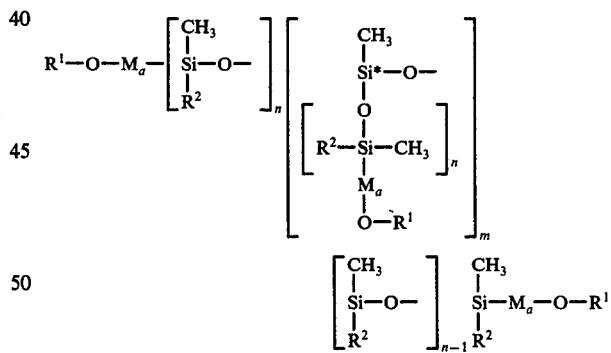

in which
R$^1$ is an alkylated phenyl residue,

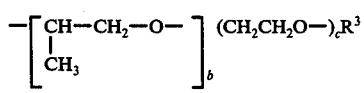

in which
R$^3$ is an alkyl residue with 1 to 16 carbon atoms, an acyl residue with 1 to 12 carbon atoms, or a hydrocarbon substituted aryl residue,
b has a value of 0 to 2, and
c has a value of 1 to 30, or
a trimethylsilyl residue, and wherein the average molecule contains 5 to 40 Si atoms, of which at most 20 mole percent are Si* atoms and 0.2 to 5 are alkylated phenyl residues which are linked directly to Si atoms via $M_a$-O bonds, and 0.2 to 5 polyether blocks, and M is a bivalent substituted hydrocarbon residue, the indices n is 2.5 to 20, m is 0 to 5, and a is 0 or 1, $R^2$ is a substituted alkyl residue with 1 to 16 carbon atoms, whose carbon chain may be interrupted by the groupings

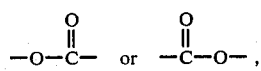

the $M_a$-O-$R^1$ residue, or the

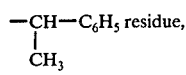

$R^4$ is an alkyl residue with 1 to 16 carbon atoms, or the

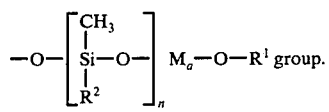

2. The compound of claim 1 which contains 10 to 25 Si atoms in the average molecule.

3. The compound of claim 1 in which $R^1$ is a mono-, di or trialkylphenyl residue wherein the sum of the carbon atoms per phenyl residue bound in the form of alkyl residues, is 6 to 12.

4. The compound of claim 3 wherein $R^1$ is an octyl, dodecyl or nonylphenyl residue.

5. The compound of claim 3 wherein the average molecule contains 0.4 to 2.0 mono-, di- or trialkylphenyl residues which are linked directly to Si atoms via $M_a$-O bonds.

6. The compounds of claim 1 wherein the average molecule contains 0.4 to 2.0 polyether blocks.

7. The compounds of claim 1 wherein n has a value of 5 to 12.5.

8. The compounds of claim 1 wherein m is 0.

9. The compounds of claim 1 wherein a is 0.

10. A melt-spin finish composition consisting essentially of:

5 to 100% by weight of the compounds of claim 1, 0 to 90% by weight of nonpolar or weakly polar oils, 0 to 30% by weight of nonionic surfactants, 0 to 15% by weight of ionic surfactants and conventional additives, whereby the sum of the constituents adds up to 100%.

11. The melt-spin finish composition of claim 10 consisting essentially of:

10 to 70% by weight of the compounds of claim 1, 40 to 90% by weight of nonpolar or weakly polar oils, 0 to 20% by weight of nonionic surfactants 0 to 10% by weight of ionic surfactants and conventional additives, whereby the sum of the constituents adds up to 100%.

12. The melt-spin finish composition of claim 10 consisting essentially of 30 to 95% by weight of a siloxane of the formula

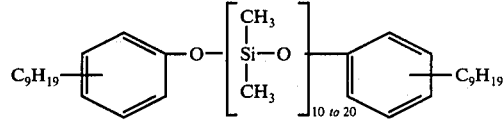

3 to 70% by weight of the compound of claim 1, and 0 to 30% by weight of $C_{12}H_{25}$-N-$(CH_2CH_2OH)_2$.

13. The melt-spin finish composition of claim 10 consisting essentially of:

8 – 95% by weight of a siloxane of the formula

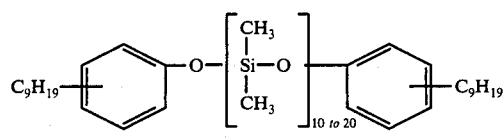

3 – 90% by weight of the compound of claim 1, 1.5 – 30% by weight of $C_{12}H_{25}$—N—$(CH_2CH_2OH)_2$; and 0.5 – 10% by weight of

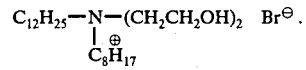

* * * * *